United States Patent [19]

Hardtmann

[11] 4,020,062
[45] Apr. 26, 1977

[54] N-(SUBSTITUTED CARBONYLMETHYL) ISATOIC ANHYDRIDES

[75] Inventor: Goetz E. Hardtmann, Florham Park, N.J.

[73] Assignee: Sandoz, Inc., E. Hanover, N.J.

[22] Filed: Jan. 3, 1975

[21] Appl. No.: 538,408

[52] U.S. Cl. .................... 260/244 A; 424/248.57; 424/248.58

[51] Int. Cl.² ............ C07D 265/00; C07D 273/00; C07D 295/00; A01N 9/00

[58] Field of Search ................ 424/248; 260/244 A

[56] References Cited

UNITED STATES PATENTS

| | | | |
|---|---|---|---|
| 2,910,488 | 10/1959 | Novello | 260/244 R |
| 3,351,659 | 11/1967 | Santilli et al. | 260/244 A |
| 3,383,415 | 5/1968 | Carabateas | 260/244 A |
| 3,725,321 | 4/1973 | Wirth et al. | 260/244 A |
| 3,729,473 | 4/1973 | Boshagen et al. | 260/244 R |
| 3,887,550 | 6/1975 | Beckwith | 260/244 A |

FOREIGN PATENTS OR APPLICATIONS

| | | |
|---|---|---|
| 2,025,248 | 12/1970 | Germany |
| 2,144,566 | 9/1971 | Germany |
| 10835-67 | 9/1963 | Japan |

OTHER PUBLICATIONS

J. of Biol. Chem. 244(II), 3009–3018, (1969)—Jovin et al.—Enzymatic Synthesis of Deoxyribonucleic Acid.

Primary Examiner—Albert T. Meyers
Assistant Examiner—D. W. Robinson
Attorney, Agent, or Firm—Gerald D. Sharkin; Richard E. Vila

[57] ABSTRACT

Isatoic anhydrides of the formula:

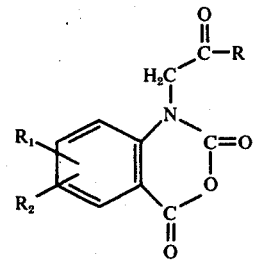

wherein R is alkyl, phenyl or phenalkyl and $R_1$ and $R_2$ are hydrogen, halo, alkyl, alkoxy or together methylenedioxy are intermediates reactable with an acyclic 5-methyl-thiopseudourea and acetonitrile to pharmaceutical agents, for example, analgetic and hypotensive agents, of the formula:

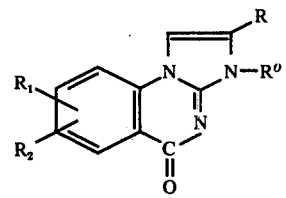

wherein R, $R_1$ and $R_2$ are as defined and $R^o$ is hydrogen, alkyl, ω-alkenyl or phenyl.

11 Claims, No Drawings

N-(SUBSTITUTED CARBONYLMETHYL) ISATOIC ANHYDRIDES

The present invention relates to isatoic anhydride intermediates useful in the preparation of imidazo[1,2-a]quinazolin-5(3H)-ones. The imidazo [1,2-a] quinazolin-5 (3H)-ones prepared from the isatoic anhydrides are useful in pharmaceutical methods and compositions based on their biological activity.

The final products prepared from the isatoic anhydride intermediates of the invention may be represented by the following structural formula I:

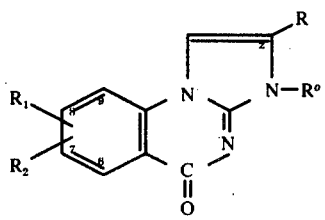

wherein
$R_1$ and $R_2$ are independently hydrogen, halo of atomic weight of from 18 to 80, i.e., fluoro, chloro or bromo, alkyl of 1 to 4 carbon atoms or alkoxy of 1 to 4 carbon atoms or $R_1$ and $R_2$ together form 7,8-methylenedioxy,
R is alkyl of 1 to 5 carbon atoms or

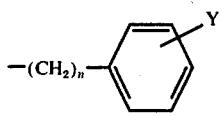

$n$ is 0, 1 or 2,
Y is hydrogen, halo of atomic weight of from 18 to 80, i.e., fluoro, chloro or bromo, alkyl of 1 to 4 carbon atoms or alkoxy of 1 to 4 carbon atoms, and
$R^0$ is hydrogen, alkyl of 1 to 6 carbon atoms, ω-alkenyl of 3 to 6 carbon atoms or phenyl,
subject to the proviso that $R_1$ and $R_2$ are both alkoxy or form methylenedioxy only when $R_0$ is phenyl.

The compounds of the formula I may be prepared by reacting a compound of the formula II:

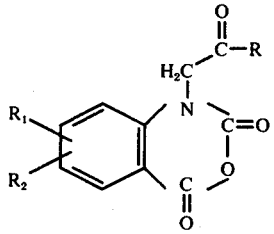

wherein R, $R_1$ and $R_2$ are as above defined, with a compound of the formula III:

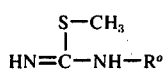

wherein $R^0$ is as above defined, and with acetonitrile, followed by heating at elevated temperatures.

The preparation of compounds I from compounds II, III and acetonitrile may be conveniently carried out in two steps. In the first step, the compounds II, III and acetonitrile are reacted at a temperature of from 40° to 95° C., preferably 60° to 90° C. While various inert organic solvents may be used, it is preferred to carry out in the reaction of the first step using excess acetonitrile as the solvent and to effect the reaction at the reflux temperature of the reaction mixture. The compound III is conveniently obtained for use in the reaction in hydrohalide acid addition salt form and neutralized in the reaction mixture by employing therein a small amount of an inorganic base such as sodium carbonate. The first step results in an intermediary product which is converted in the second step by heating said intermediary product to a temperature of from at least about 100° to 200° C., preferably 130° to 180° C. The second step is typically carried out by first isolating the intermediary product and dissolving it in a suitable high boiling inert organic solvent such as diglyme, and then effecting the second step at the reflux temperature of the resulting reaction mixture. In general, the intermediary product may be isolated and the desired product of the formula I recovered by working up by established procedures.

While it is not desired to be limited to any particular mechanism by which the compounds I are prepared from the above-described reaction, it is indicated that such preparation involves the following reaction scheme:

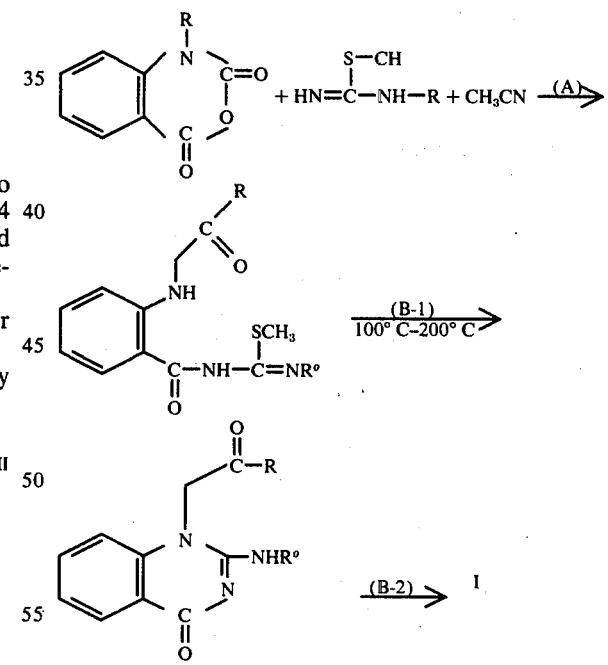

wherein A is the first step reaction and B-1 and B-2 are the stages by which the second step proceeds to form the desired products of the formula I.

The compounds of the formula III are either known or may be prepared by procedures established for the known compounds.

The compounds of the formula II are novel and valuable intermediates also provided by the present invention and may be prepared by reacting a compound of the formula IV

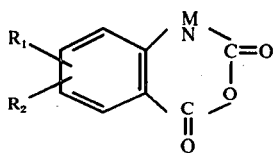

in which $R_1$ and $R_2$ are as defined and M is hydrogen or an alkali metal, with a compound of the formula V:

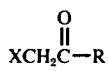

in which R is as defined and X is halo, e.g., chloro or bromo.

The preparation of compounds II from compounds IV and V may be carried out at temperatures of from 0° to 100° C., preferably 20° to 50° C. The reaction is conveniently effected in an inert organic solvent which may be of conventional type, e.g., dimethylacetamide. The reaction is preferably effected with a compound IV in which M is an alkali metal and such compounds are prepared in a conventional manner by reacting a compound in which M is hydrogen with a strong base such as an alkali metal hydride, e.g., sodium hydride. If the compound IV in which M is hydrogen is employed, the reaction is carried out in the presence of a strong base, e.g., an alkali metal alkoxide or hydroxide.

The compounds of formulae IV and V are either known or may be prepared from known materials by established procedures.

The compounds of the formula I in which $R^0$ is phenyl are useful as hypotensive agents, e.g., as antihypertensive agents, agents as indicated by a lowering of blood pressure upon intravenous administration to an anesthetized dog at a dosage of 1–20 mg/kg body weight and upon oral administration to a hypertensive unanesthetized rat at a dosage of 10–200 mg/kg body weight.

The anesthetized dog test involves the intravenous administration of the test compound and the measurement of the resulting effect on the blood pressure of the test animal with the aid of a mercury manometer or transducer via a catheter inserted in either the carotid or the femoral artery of the anesthetized animal and recorded on a kymograph or an appropriate electronic recorder. The surgical method of preparing the animal is a modification of that described by Markowitz (Exper. Surgery, 2nd ed., Williams and Wilkins, Baltimore, Md. (1949)).

The unanesthetized rat test involves preparing the rats by implanting subcutaneously in weanling rats two pellets, each containing 25 mg. of deoxycorticosterone acetate (DOCA) and replacing their drinking water with 0.2% saline. After 4 to 6 weeks the rats are sufficiently hypertensive for use. The compound is administered orally to the rats and their blood pressure is monitored by pneumatic pulse transducer.

The precise dosage of the compound of formula I to be employed depends upon several factors including the mode of administration and the particular compound employed. In general, a daily dosage of 1–200 mg/kg body weight, with a daily dosage of 200–2000 mg. for most larger mammals, gives satisfactory results. In general, oral administration requires a higher dose than does intravenous administration. Usually, small dosages are administered initially with a gradual increase in dosage until the optimal dosage for the host under treatment is determined. The daily dosage is usually divided into two to four equal portions and dosage forms for oral administration generally comprise from 50 to 1000 milligrams of the compound in combination with an inert pharmaceutically acceptable carrier.

The compounds of the formula I in which $R^0$ is alkyl or ω-alkenyl are useful as mild non-narcotic analgesic agents as indicated by the Writhing method tests in mice according to the procedure of Seigmund et al., Proc. Soc. Exp. Biol., 95: 729 (1957) on administration orally (50–400 mg./kg.). For such use and depending upon known factors satisfactory results are generally obtained on the daily administration of from 6 to 400 milligrams per kilogram of body weight, preferably given orally and in divided doses two to four times a day. For most mammals, the administration of from 400 to 2000 milligrams per day provides satisfactory results and dosage forms suitable for internal administration comprise from 100 to 1000 milligrams of such a compound in admixture with a solid or liquid pharmaceutical carrier.

The compounds of formula I may be formulated into conventional pharmaceutical compositions and administered by conventional modes of administration.

The compounds may be combined with pharmaceutically acceptable carriers and other conventional pharmaceutical adjuvants and administered orally in the form of tablets, dispersible powders, granules, capsules, elixirs, suspensions and the like or parenterally in the form of an injectable solution or suspension. The compositions may be prepared by conventional means and may contain one or more conventional adjuvants such as sweetening agents (oral compositions only), other flavoring agents (oral compositions only), coloring agents (oral compositions only) and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and adsorption in the gastro-intestinal tract and thereby provide a sustained action over a longer period.

Capsules may contain the compound of formula I alone or admixed with an inert solid diluent, e.g., calcium carbonate, calcium phosphate, kaolin, lactose and high molecular weight polyethylene glycols.

Suspensions, syrups and elixirs may contain a compound of formula I in admixture with any of the conventional excipients utilized for the preparation of such compositions, i.e., suspending agents, e.g., methylcellulose, tragacanth and sodium alginate, wetting agents, e.g., lecithin, polyoxyethylene, stearate and polyoxyethylene sorbitan monooleate, preservatives, e.g., ethyl p-hydroxybenzoate, and diluents, e.g., ethanol, propylene glycol and glycerin.

Injectable compositions may contain glucose or salt and should, if necessary, be buffered to render them isotonic.

The preferred pharmaceutical compositions from the standpoint of ease of preparation and administration are solid compositions and particularly hard-filled capsules.

A representative formulation prepared by conventional techniques for encapsulation in a hard gelatin capsule and useful in treating hypertension on administration four times a day is:

| Ingredients | Weight (mg.) |
|---|---|
| 2-methyl-3-phenyl-imidazo [1,2-a]quinazolin-5(3H)-one | 100 |
| Lactose | 200 |

The following examples show representative compounds encompassed by this invention and a process for their synthesis. However, it is to be understood that they are for purposes of illustration only.

EXAMPLE 1

2,3-dimethyl-imidazo[1,2-a]quinazolin-5(3H)-one

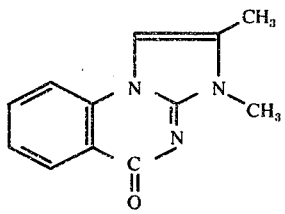

STEP A: Preparation of N-methylcarbonylmethyl isatoic anhydride

A mixture of 50 g. of isatoic anhydride, 14 g. of pentane washed sodium hydride and 500 ml. of dimethylacetamide is stirred for 1 hour at room temperature and there is then added 30 g. of chloroacetone followed by stirring at room temperature for 12 hours. The resulting mixture is evaporated to one third its volume, cooled and poured over 600 ml. of ice water. The resulting precipitate is recovered by filtering, water washed, dried under reduced pressure and dissolved in 500 ml. of methylene chloride. The resulting solution is dried, treated with carbon, filtered through celite, the methylene chloride exchanged for ether and the resulting precipitate recovered by filtering, washed with ether and dried under reduced pressure to obtain N-methylcarbonylmethyl isatoic anhydride, m.p. 154°–157° C.

STEP B: Preparation of 2,3-dimethyl-imidazo[1,2-a]quinazolin-5(3H)-one

A mixture of 11.0 g. of N-methylcarbonylmethyl isatoic anhydride, 16.6 g. of S,N-dimethyl-thiopseudourea hydroiodide, 5.5 g. of sodium carbonate and 150 ml. of acetonitrile is refluxed for one-half hour, filtered, evaporated to dryness, the residue dissolved in methylene chloride and evaporated again to dryness. The residue is taken up in diglyme, refluxed for one-half hour and cooled with stirring to obtain a precipitate which is recovered by filtering, washed with ether, dissolved in methylene chloride, treated with carbon, alumina and sodium sulfate, filtered through celite, and the methylene chloride exchanged for ether. The resulting precipitate is recovered by filtering, washed with ether and dried under reduced pressure to obtain 2,3-dimethyl-imidazo[1,2-c]quinazolin-5(3H)-one, m.p. 234°–237° C.

EXAMPLE 2

Following the procedure of Step A of Example 1 the following are prepared:
A. N-phenylcarbonylmethyl isatoic anhydride, m.p. 211°–213° C.,
B. N-t-butylcarbonylmethyl isatoic anhydride, m.p. 140°–142° C.,
C. N-methylcarbonylmethyl-7-chloro isatoic anhydride,
D. N-benzylcarbonylmethyl isatoic anhydride,
E. N-methylcarbonylmethyl-6,7-methylenedioxy isatoic anhydride,
F. N-methylcarbonylmethyl-6,7-dimethoxy isatoic anhydride
G. N-phenethylcarbonylmethyl isatoic anhydride,
H. N-(4'-fluorobenzylcarbonylmethyl) isatoic anhydride, and
I. N-(4'-methoxyphenylcarbonylmethyl) isatoic anhydride, which are employed in preparation of the following compounds of the formula I:
A-1. 2-phenyl-3-allyl-imidazo[1,2-c]quinazolin-5(3H)-one, m.p. 198°–201° C.
A-2. 2,3-diphenyl-imidazo[1,2-c]quinazolin-5(3H)-one,
B-1. 2-t-butyl-3-phenyl-imidazo[1,2-c]quinazolin-5(3H)-one,
B-2. 2-t-butyl-3-n-butyl-imidazo[1,2-c]quinazolin-5(3H)-one, m.p. 163°–165° C.
C-1. 7-chloro-2-methyl-3-n-butyl-imidazo[1,2-c]quinazolin-5(3H)-one, m.p. 231°–234° C.,
D-1. 2-benzyl-3-methyl-imidazo[1,2-c]quinazolin-5(3H)-one,
E-1. 2-methyl-3-phenyl-7,8-methylenedioxy-imidazo[1,2-c]quinazolin-5(3H)-one.
F-1. 2-methyl-3-phenyl-7,8-dimethoxy-imidazo [1,2-c]quinazolin-5(3H)-one,
G-1. 2-phenethyl-3-n-butyl-imidazo[1,2-c]quinazolin-5(3H)-one,
H-1. 2-(4'-fluorobenzyl)-3-n-butyl-imidazo [1,2-c]quinazolin-5(3H)-one, and
I-1. 2-(4'-methoxyphenyl)-3-phenyl-imidazo [1,2-c]quinazolin-5(3H)-one.

EXAMPLE 3

Following the procedure of Step B of Example 1 there is also prepared:
A. 2-methyl-3-allyl-imidazo[1,2-c]quinazolin-5(3H)-one, m.p. 223–226° C.
B. 2-methyl-3-phenyl-imidazo[1,2-c]quinazolin-5(3H)-one, m.p. 237°–238° C.

What is claimed is:
1. A compound of the formula:

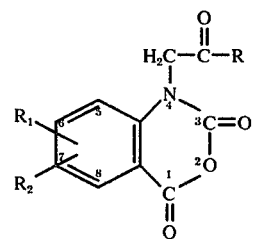

wherein
R₁ and R₂ are independently hydrogen, fluoro, chloro, bromo, alkyl of 1 to 4 carbon atoms or alkoxy of 1 to 4 carbon atoms or R₁ and R₂ together form 7,8-methylenedioxy,
R is alkyl of 1 to 5 carbon atoms or

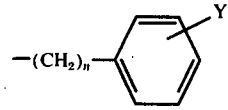

n is 0, 1 or 2, and
Y is hydrogen, fluoro, chloro, bromo, alkyl of 1 to 4 carbon atoms or alkoxy of 1 to 4 carbon atoms.
2. A compound of claim 1 in which R is alkyl.
3. A compound of claim 1 in which R is

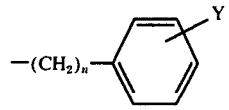

4. A compound of claim 3 in which n is 0.
5. A compound of claim 3 in which n is 1.
6. A compound of claim 1 in which R₁ and R₂ are hydrogen.
7. The compound of claim 6 in which R is methyl.
8. The compound of claim 6 in which R is t-butyl.
9. The compound of claim 4 in which R₁ and R₂ are hydrogen and Y is hydrogen.
10. The compound of claim 5 in which R₁ and R₂ are hydrogen and Y is hydrogen.
11. The compound of claim 2 in which R is methyl, R₁ is 7-chloro and R₂ is hydrogen.

* * * * *